United States Patent [19]

Ishida et al.

[11] Patent Number: 5,166,067
[45] Date of Patent: Nov. 24, 1992

[54] CULTURING METHOD, SYSTEM AND APPARATUS FOR CELL CULTURE

[75] Inventors: Masahiko Ishida; Ryoichi Haga; Harumi Matsuzaki, all of Hitachi, Japan

[73] Assignee: Hitachi, Ltd., Tokyo, Japan

[21] Appl. No.: 443,108

[22] Filed: Nov. 29, 1989

[30] Foreign Application Priority Data

Nov. 30, 1988 [JP] Japan .................. 63-300968

[51] Int. Cl.$^5$ .......................... C12N 5/02; C12N 5/00; C12M 3/02; C12M 3/06
[52] U.S. Cl. .................. 435/240.25; 435/286; 435/311; 435/240.1
[58] Field of Search .............. 435/285, 286, 311, 312, 435/240.2, 240.25, 240.1; 210/409, 410, 411, 650, 651, 652

[56] References Cited

U.S. PATENT DOCUMENTS

| | | | |
|---|---|---|---|
| 3,898,045 | 8/1975 | Bowley | 435/285 |
| 4,177,138 | 12/1979 | Mastuzaki et al. | 210/410 |
| 4,335,215 | 6/1982 | Tolbert et al. | |
| 4,426,450 | 1/1984 | Donofrio | 435/243 |
| 4,775,471 | 10/1988 | Nagai et al. | 210/409 |
| 4,833,078 | 5/1989 | Hsieh | 435/253.3 |
| 4,900,669 | 2/1990 | Hatch et al. | 935/56 |

FOREIGN PATENT DOCUMENTS

| | | |
|---|---|---|
| 0201086 | 11/1986 | European Pat. Off. ........ 435/240.25 |
| 224734A1 | 6/1987 | European Pat. Off. . |
| 336966 | 10/1989 | European Pat. Off. . |
| WO 86/07605 | 12/1986 | PCT Int'l Appl. . |

OTHER PUBLICATIONS

"The Large-Scale Cultivation of Mammalian Cells", Joseph Feder et al., Scientific American, Jan., 1983.

*Primary Examiner*—Howard E. Schain
*Assistant Examiner*—George C. Elliott
*Attorney, Agent, or Firm*—Fay, Sharpe, Beall, Fagan, Minnich & McKee

[57] ABSTRACT

A culturing method and system are disclosed in which a cell culture broth in withdrawn from a culturing apparatus to a filteration apparatus. The withdrawn broth in brought into contact with a membrane for precision filteration. Then a non-toxic gas is brown into the broth, while filtering the broth to separate the cells and breaking foams occurring on the surface of the broth due to gas bubbling. The separated cells are returned to the vessel and the filterate is withdrawn from the filteration apparatus.

The method and system have such advantages that a perfusion culture of a long period of time can be realized because the clogging of the filtration membrane is effectively prevented.

10 Claims, 2 Drawing Sheets

CULTURING METHOD, SYSTEM AND APPARATUS FOR CELL CULTURE

BACKGROUND OF THE INVENTION

1. Field of the Invention

This invention relates to a culturing method of living cells and more particularly to a method for a large scale, high concentration culturing, a culturing system and a culturing apparatus of living cells which perform suspension culture of living cells in a liquid medium and efficiently remove waste components.

2. Description of the Prior Art

Recently, the production of a monoclonal antibody and interferon by the culture of animal cells and the production of natural pigments by vegetable cells have been started in addition to the culture of microorganism cells. To produce such useful materials on an industrial basis, so-called "high density culture" by which cells can be cultured on a large scale for a long period of time while keeping them stable under a high concentration becomes necessary.

Nutrient components are consumed while waste components such as lactate and the like are generated in a culture tank during the cell propagation process and if this condition is left standing as such, the propagation of the living cells is impeded and high density culture is not attained. Therefore, so-called "perfusion culture" is essential, according to which separates the cells in the culture broth, removes the cell-free waste solution to the outside of the system and exchanges with a fresh medium.

Since the cell is a kind of particles, which have a greater specific gravity than that of the medium, a perfusion culturing method which applies a heretofore solid-liquid separation technique is known. As the separation methods of cells, sedimentation separation, centrifugal separation and membrane filteration are ordinarily employed. A membrane filteration device is disposed in a culture tank of a culturing apparatus or outside the culturing apparatus. This is described, for example, in Scientific American 248 (1) p. 24 (1983) and in Japanese Patent Laid-Open No. 102187/1985.

The studies of these conventional methods by the present inventors revealed that if a membrane filtration device is disposed in the culturing apparatus, the cells attached to the membrane surface propagate to bring about irreversible clogging. Moreover, once the culture is started, the exchange of the filtration device is not possible during the culturing period and since the structure and position of the filtration device affects greatly mixing the solutions in the culturing apparatus and the supply of oxygen, scale-up of the culture apparatus is difficult to attain.

The latter two problems can be solved by disposing the filtration device outside the culturing apparatus, but it has been found that if the filtration device is simply disposed outside the culturing apparatus and ordinary back-wash is simply carried out, it is difficult to conduct perfusion-culture for a long period of time without clogging of the film particularly under a high concentration of $1 \times 10^7$ cells/ml or more.

SUMMARY OF THE INVENTION

Object of the Invention

It is an object of the present invention to provide a culturing method, system and apparatus for cell culture which eliminates damage to living cells and are free from contamination of culture broth due to bacteria.

Statement of the Invention

The present invention produces a high density culture for a long period of time by development of a novel filtration device capable of avoiding clogging of the film.

That is, the present invention provides a culturing method of living cells comprising:
withdrawing a cell culture broth from a culturing apparatus;
bringing a membrane for precision filtration into contact with the culture broth thus withdrawn;
performing precision filteration of said culture broth by way of said membrane, while bringing a gas which is non-toxic to the cell into contact with a surface of the membrane immersed in said culture broth;
rupturing foams occurring on the liquid surface by a defoaming layer made of a hydrophobic material and disposed on the liquid surface;
returning the cells thus separated into said culturing apparatus; and
withdrawing the filtrate from said culturing apparatus.

The present invention also provides a culturing system for living cells, which comprises:
(a) a culturing apparatus having a vessel for culturing cells in the suspension state in a culture broth;
(b) means for supplying the cells into the vessel;
(c) means for supplying a medium into the vessel, thereby to form the culture broth;
(d) means for withdrawing a part of the culture broth from the vessel;
(e) means for transferring the withdrawn culture broth to a filtration apparatus having a membrane for precision filtration;
(f) means for blowing a gas which in non-toxic to the cells into the culture broth which is in contact with the membrane of the filtration apparatus;
(g) means for breaking foams occurring on the surface of the culture broth in the filtration apparatus;
(h) means for returning the cells separated in the filtration apparatus to the vessel; and
(i) means for withdrawing the filtrate from the filtration apparatus.

DETAILED DESCRIPTION OF THE INVENTION

Figure 1:
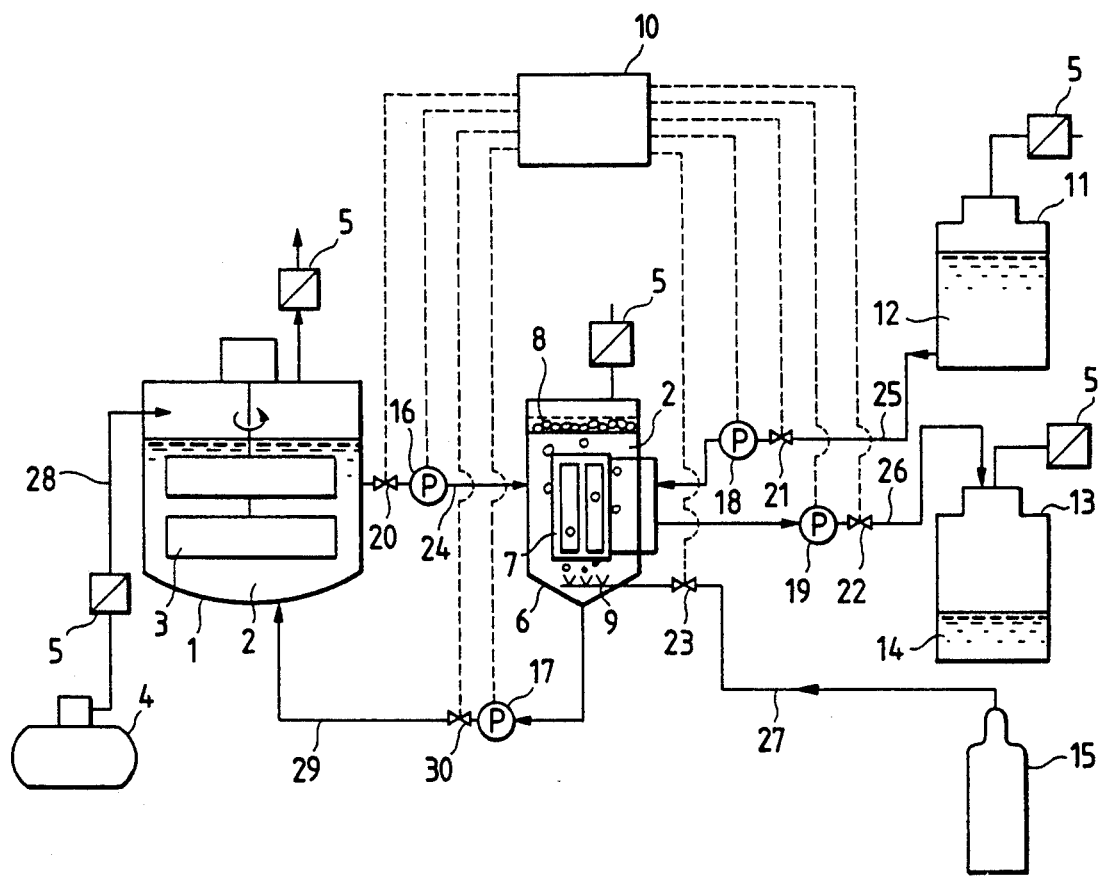
FIGS. 1 and 2 are culturing system views in accordance with embodiments of the present invention.

A feature of the present invention resides in that a cell culture broth in a culturing apparatus is withdrawn to the outside of the apparatus, the withdrawn culture broth is subjected to filtration using a filtration while a gas which is non-toxic to cells is in contact with the membrane under a reduced pressure so that the cells are separated from the liquid and returned into the culturing apparatus. Since filtration is made while the gas is in contact with the membrane surface, clogging of the filtration membrane due to cell propagation on the membrane surface is minimized. If the gas is not brought into contact with the membrane surface, the cells adhering to the membrane surface propagate and clog the pores of the membrane so that a pressure loss increases drastically and filtration becomes impossible.

In the present invention, protein-containing foams which are difficult to be broken formed by the gas blown thereinto on the liquid surface are effectively ruptured by a defoaming layer made of a hydrophobic material so that the filtration process can be continued. In addition to the proteins such as serum and albumin contained in the medium, those proteins which are excreted by the cells are contained in the culture broth. Theredire, blowing a gas into the broth without foaming is almost impossible.

In the present invention, besides an outer tubular membrane for precision filtration, an inner tubular membrane for molecular filtration is disposed in the outer tubular membrane to form a two-layered membrane having a gap between both membranes so that the pressure at the inner surface of a molecular filtration membrane is kept the same as, or near to the pressure of the inner surface of the precision filtration membrane in order to extract only a low molecular weight filtrate, when the pressure in the molecular filtration membrane is reduced. The low molecular weight filtrate and a filtrate containing a polymer can be separated from one another, when a pressures in the molecular filtration membrane and the precision filtration membrane are reduced. A low molecular weight nutrient solution from only the inner surface of the molecular filtration membrane or to the inner surfaces of both membranes are supplied under pressure at the time of back-wash. According to this arrangement, the low molecular weight waste components can be altogether removed by a single filtration apparatus and back-wash of both films can be made simultaneously. Furthermore, it is possible to recover and re-utilize serum and growth factors which are excreted from cells. If the gap is defined between both membranes, the precision filtration membrane can be back-washed and regenerated simultaneously and effectively from the inner molecular filtration membrane side.

In the present invention, the drastic increase of the cell concentration in the filtration apparatus is restricted by filtering a culture broth while flowing into the filtration apparatus, and then the concentrated suspension of the cells generated by back-wash after filtration is sent back to the culture tank.

In other words, if the bottom of the filtration apparatus and the culture tank are connected by a piping arrangement and a gas is blown into the filtration apparatus from a sparger disposed at the bottom of the filtration apparatus, it becomes possible not only to prevent adhesion of the cells to the membrane surface and their propagation on the membrane surface and inside the membrane matrix but also to return the solution in the filtration apparatus into the culture tank due to the gas lift effect and to introduce the culture broth in the culture tank into the filtration apparatus. Accordingly, it is possible to mitigate the rise of the cell concentration at the time of filtration, and to extend the life of the filtration membrane as well as to effectively return the cell aggregate occurring at the time of film filtration to the culture tank. In this case, the gas that is introduced into the filtration apparatus passes through the bottom of the culture tank and forms bubbles on the liquid surface of the culture tank. Therefore, the defoaming layer which is the same as the one used in the aforementioned filtration apparatus is disposed on the liquid surface of the culture tank. Besides the measures described above, two piping arrangements for connecting the filtration apparatus and the culturing apparatus are prepared, one of which is used for transferring the culture broth from the culture tank to the filtration apparatus at time of filtration. A valve and a pump are fitted into the other piping arrangement through which the culture broth in the culture tank is transferred to the bottom of the filtration apparatus at a linear speed of at least 2 cm/sec and in a volume at least 50% of the charged solution quantity of the filtration apparatus at the time of back-wash of the membrane or after the back-wash. The concentrated suspension of the cells occurring at the time of back-wash is returned to the culture tank.

The living cells to which the present invention is applied are not particularly limited, and include animal cells, plant cells and microorganism cells. The animal cells include, for example, various cells of vertebrates and invertebrates. The cells:

May be not only a single cell but also a cell aggregate.

The plant cells include the cells and cell aggregates of higher plants and the cells and cell aggregates of algae.

The culturing method and the culturing apparatus for the method are not particularly limited, either, but are primarily suitable for the cells under the suspended state. In the case of the suspension culture wherein cells are supported on carriers such as microbeads and gel particles for immobilization of cells, there are many cells that fall off from the carrier particles and the cells are suspended in the solution. Accordingly, these culturing methods, conditions, culturing apparatuses (culture tanks), etc., are selected in accordance with the cells used, the object of the culture, the scale and the control method. Particularly, the temperature, pH, the dissolved oxygen concentration, the dissolved carbonic acid concentration, the oxidation-reduction potential, etc., are controlled suitably in accordance with the intended object.

Membranes having a pore diameter capable of separating the intended cells are suitably selected. The pore diameter is preferably from 5 $\mu$m to 0.5 $\mu$m. Heretofore, known materials such as acetyl cellulose or poly-tetrafluoroethyrene can be used sufficiently as the membrane material. Though the shape of the membrane, is selected suitably, a hollow fiber module is suitable in order to increase the surface area of the membrane and to provide a liquid transfer port. The filtrate can be extracted conveniently by gathering both ends of a plurality of hollow fibers but can be extracted by connecting both ends to form a loop and extracting the filtrate from a suitable position of the loop or by closing one of the ends and gathering the other end of each hollow fiber so as to extract the filtrate from the bundled tubes.

Filtration under reduced pressure is ordinarily used as the filtration system. If filtration under elevated pressure is carried out, it must be carried out in consideration of the drop of pH due to dissolution of the carbon dioxide gas in the solution and of damage of brittle cells. The direction of the membrane surface inside the filtration apparatus is not particularly limitative, and its arrangement and structure are selected so that the bubbles come efficiently into contact with the membrane surface. For example, the direction of the hollow fibers are disposed either vertically or horizontally. The air flowing method is not particularly limitative, either but a flow of at least 0.1 ml/min per $cm^2$ surface area of membrane is necessary. The diameter of bubbles is selected suitably to be 1 to 10 mm, for example. The gas to be blown is selected suitably from among those which are not toxic to the cells. Examples include nitrogen, argon and air. The filtration pressure is selected suitably in accordance with the material, the solution, the cell concentration, the operating conditions, and the like, and is suitably from $0.01 \sim 5$ kg/cm$^2$.

Defoaming of the foams on the liquid surface is made by the defoaming layer disposed on the surface of the liquid. The defoaming layer has a large number of openings capable of passing the gas and its open ration is preferably at least 50% and a diameter of opening is preferably from 2 to 50 mm. At least the surface of the defoaming layer is made of a hydrophobic material which forms a contact angle of at least 80' with the culture solution or the liquid of the medium. A suitable example is an organic polymer of silane or siloxane having a carbon number of at least 10. Though the defoaming layer may be used as a single layer or a plurality of layers, the latter being preferable in consideration of the drop of water repellency of the hydrophobic surface due to the deposition of the cells for the operation for a long period. The drop of water repellency of the defoaming layer can be recovered with washing its surface by the culture filtrate, the medium or the culture broth.

As described above, the culture broth in the culturing apparatus is withdrawn outside the apparatus, the gas is brought into contact with the filtration membrane immersed in the culture broth thus withdrawn and filtration under reduced pressure is carried out to separate the cells and to return them back into the culturing apparatus. If filtration is conducted without the contact of the gas, the cells that enter the membrane matrix and adhere thereto propagate gradually to clog the pores of the membrane so that clogging proceeds irreversibly even if back-wash is conducted by use of the liquid culture medium or the like as the washing solution. The pressure drop increases drastically at the time of filtration, and at last filtration becomes impossible. Animal cells are likely to adhere to the membrane or to the other cells, leading to clogging of the membrane. In contrast, if filtration is carried out while the gas is brought into contact with the membrane, adhesion of the cells to the membrane surface and the propagation of the cells on the surface and the matrix can be completely prevented so that clogging of the membrane can be prevented. Accordingly, if filtration and back-wash are cyclically carried out regeneration and use of the membrane can be made reversibly for a period as long as one month or more.

EXAMPLES

Next, the present invention will be described in further detail with reference to embodiments thereof.

EXAMPLE 1

Perfusion culture of animal cells was carried out by use of a culturing system shown in FIG. 1.

Prior to the culture, steam was supplied to each tank of the system and to each piping arrangement to heat them at 125° C. for at least 30 minutes for sterilization. A medium having the following composition was charged under the microorganism-free condition into a culture tank 11.
Eagle MEM medium (a product of
Nissui Seiyaku K. K., Eagle MEM
Nissui ①): 9.4 g/l
glutamine: 0.92 g/l
7.5% aqueous solution of sodium hydrocarbonate: 29 ml/l
glucose: 20 g/l
bovine serum: 100 ml/l.

Rat liver cancer cell JTC-1 (Japan Tissue Culture No. 1) was used as the seed cells. The suspension of the seed cells used for the culture was prepared in the following way.

Five milliliters of the medium described above was charged dividedly into each of 15 flat flasks having a capacity of 20 ml and the JTC-1 strain described above was inoculated and subjected to setting culture in a concentration of $1 \times 10^5$ cells/ml. After culturing for three days, the cells adhering to the inner surface of the flask were peeled and joined with the cells suspended in the solution to obtain 75 ml of the culture solution having a cell concentration of $4.0 \times 10^5$ cells/ml. This culture solution was charged under a microorganism-free condition and dividedly into a centrifugal tube which was treated under a microorganism-free condition, and the cells were recovered by a suspension type open centrifuge. The cells were innoculated to two 1-l roller bottles containing 75 ml of the medium and cultured at 37° C. for three days. This operation was repeated several times to increase the quantity of the culture broth to obtain 2 l of the culture broth having a concentration of $1.0 \times 10^6$ cells/ml. The cells are recovered from this culture broth in the manner described above and suspended in 500 ml of the medium to obtain the seed cell suspension.

In the culturing system, a membrane filtration-apparatus 6, the culturing apparatus 1, a medium tank 11 and a culture filtrate tank 13 are connected by liquid transfer piping arrangements 24, 25, 26 and 29. A valve and a liquid transfer pump on each liquid transfer piping arrangement are connected to a process sequencer 10.

The culture tank has an effective capacity of 5 l and is made of a stainless steel. A temperature, pH and DO besides a stirrer 3 are automatically controlled. Oxygen is supplied in an overlay method to the liquid surface of the culture tank from a compressor 4 by an air transfer piping arrangement 28 through an air filter 5. Oxygen is dissolved by diffusion from the liquid surface and supplies dissolved oxygen necessary for the propagation of the cells.

After 4.5 l of the medium, which was the same medium used in seed the culture, was introduced under a microorganism-free condition into the culturing apparatus that was steam treated, 0.5 l of the seed cell suspension described above was inoculated to the medium thereby to adjust the cell concentration to $4.1 \times 10^5$ cells/ml. While microbial free air was blown at a rate of $10 \sim 30$ l/min from the side wall of the tank onto the liquid surface, the culture was carried out at a stirring speed of 20 r.p.m., 37° C. and pH of $7.0 \sim 7.6$. The flow-rate of air was adjusted automatically so that the dissolved oxygen concentration (DO) in the culture solution became 1 ppm.

One-liter of the culture broth 2 was transferred to the filtration apparatus 6 by opening the valve 20 and operating the pump 16. The filtration apparatus 6 has an effective volume of 1.3 l and is made of a stainless steel. A hollow fiber module of a precision filtration membrane 7 is disposed in the culture broth. Five hollow fiber membranes, which are made of tetrafluoroethylene have an outer diameter of 2 mm, an inner diameter of 1 mm and a pore diameter of 0.8 μm and are 1 m long, are juxtaposed and both terminals are gathered to a common piping arrangement. Furthermore, both piping arrangements are connected to the medium tank 11 by a medium transfer piping arrangement 25 and to the culture filtrate tank 13 by a culture filtrate transfer piping arrangement 26. A sparger 9 (diameter 30 mm; ring sparger; 10 holes of diameter 1 mm) is disposed at the bottom of the filtration apparatus 6 so that bubbles of nitrogen gas can be brought into contact with the precision filtration membrane 7 from a pressure vessel 15 through a gas transfer piping arrangement 27. A defoaming layer 8 is disposed on the liquid surface. The defoaming layer 8 is a stainless steel net (one side of mesh: 3 mm) having a rectangular mesh which is formed by thinly coating a silane type organic polymer (viscosity: $1 \times 10^5$ cps) on its surface. A piping arrangement 29 is disposed at the bottom of the tank in order to return the cell suspension obtained after filtration and back-wash into the culture tank 1.

Nitrogen gas was ventilated from the sparger towards the precision filtration membrane at a rate of 100 ml/min while culture broth 2 was introduced into the filtration apparatus 1 and the filtrate 14 was withdrawn by the pump 19 while breaking the resulting foams by the defoaming layer and was transferred to the filtrate storage tank 13. The filtration speed was set to 0.5 l/h and filtration was stopped when the filtrate quantity reached 0.5 l/h. Next, 0.5 l of a fresh medium 12 in the medium tank 11 was pressure-fed as the back-wash solution into the precision filtration membrane 3 at a rate of 3 l/h through the piping arrangement 25. The resulting cell suspension was returned back to the culturing apparatus 1 by the pump 17 through the piping arrangement 29. This process was carried out 10 cycles/day and the culture was continued for 30 days. The viable cell concentration and the survival ratio in the culturing apparatus 1 and the pressure loss at the time of filtration in this instance are tabulated in Table 1 below.

Since the survival ration (viable cells/total cells $\times 100$) of the cells during the culture was as high as 90% or more and the pressure drop of membrane filtration did not increase, it can be understood that the present system can culture the cells efficiently without clogging the membrane.

TABLE 1

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 4.1 | 4.1 | 4.6 | 12 | 36 | 70 | 75 |
| Survival ratio (%) | 90 | 91 | 91 | 92 | 91 | 92 | 91 |
| Pressure drop at time of filtration (kg/cm$^2$) | −0.05 | −0.05 | −0.05 | −0.05 | −0.06 | −0.05 | −0.06 |

EXAMPLE 2

Perfusion culture of animal cells was carried out by use of the culturing system in which the same medium and the animal cells of the same kind as those of Example 1 were used. A cell suspension prepared by centrifuging 2 l of a culture broth of $1.0 \times 10^6$ cells/ml and suspending the cells in the medium in the same way as in Example 1 was used as the seed cell suspension.

In this culture, a medium spray nozzle for washing the defoaming layer 8 is added to the upper part of the defoaming layer of the filtration-apparatus 6 of the system used in Example 1. The spray nozzle is the same type as the sparger 9.

While the same quantity of the medium as the filtrate quantity was used for back-wash in Example 1,480 ml for back-wash was used in this example. The medium was also used for washing the defoaming layer (400 ml/min, 0.5 min.) once a day.

The culture was carried out in the same way and under the same operation condition as those of Example 1. The result is tabulated in Table 2. The cells exhibited substantially the same type of propagation with a high survival ratio as in Example 1.

TABLE 2

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 4.1 | 4.1 | 4.6 | 13 | 35 | 72 | 76 |
| Survival ratio (%) | 91 | 91 | 92 | 92 | 91 | 92 | 91 |
| Pressure drop at time of filtration (kg/cm$^2$) | −0.05 | −0.05 | −0.05 | −0.05 | −0.05 | −0.06 | −0.05 |

EXAMPLE 3

Perfusion culture of animal cells was carried out by use of the culturing system in which the same medium and the animal cells of the same strain as those of Example 1 were used. As the seed cell suspension, 2 l of culture broth having a concentration of $1.0 \times 10^6$ cells/ml, which was prepared under the same operation condition as in Example 1, was centrifuged so as to separate the cells and the cell suspension prepared by suspending the resulting cells in the medium was used as the seed cell suspension.

This culturing system was the same as the system of Example 1 except that one of the ends of the hollow fibers of the precision filtration membrane 7 of the filtration-apparatus 6 were closed, and the other ends of the hollow fibers were communicated and connected to the piping arrangement. The culture was carried out in the same way and under the same condition as those of Example 1. The results are tabulated in Table 3 below. Substantially the same propagation was observed with a high survival ratio as in Example 1.

TABLE 3

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 3.9 | 4.1 | 4.7 | 14 | 35 | 75 | 79 |
| Survival ratio (%) | 91 | 91 | 91 | 92 | 92 | 92 | 92 |
| Pressure drop at time of filtration (kg/cm$^2$) | −0.05 | −0.05 | −0.05 | −0.05 | −0.05 | −0.05 | −0.05 |

EXAMPLE 4

Perfusion culture of animal cells was carried out by the culturing system in which the same medium and the animal cells of the same strain as those of Example 1 were used. However, the serum was added to 4.5 l of the medium at the start of the culture to be 10% concentration and no addition was made to the medium after the culture was started. The cell suspension prepared by centrifuging 2 l of the culture broth having a concentration of $1.0 \times 10^6$ cells/ml, that was prepared under the same operation condition as in Example 1, and suspending the cells thus separated in the medium was used as the seed cell suspension.

In this culturing system, the filtration membrane of the filtration-apparatus 6 was two-layered hollow fiber membranes formed by disposing molecular filtration membranes (not shown) inside the precision filtration membranes with a gap therebetween. During filtration, the pressure of the inner surface of the molecular filtration membrane was kept at a level lower than that of the inner surface of the precision filtration membrane so that the low molecular weight filtrate could be withdrawn from inside the molecular filtration membrane and the filtrate containing polymers was withdrawn from between the precision filtration film 7 and the molecular filtration membrane separately from each other. The low molecular weight filtrate was sent back to the low molecular weight filtrate tank 13 while the polymer-containing filtrate was sent back by the pump (not shown) to the culturing apparatus 1 through the piping arrangement connected to the pump. The precision filtration membrane had the following structure. The hollow fiber of the same material as that of Example 1 and having an outer diameter of 3 mm, an inner diameter of 2 mm and the same length was used, and a hollow fiber membrane for molecular filtration (pore diameters: 6,000 Dalton) made of acetyl cellulose and having an outer diameter of 1 mm and an inner diameter of 0.5 mm was inserted into the hollow fiber described above to form a hollow double-layered pipe. Both ends of the films were gathered to the same withdrawal ports so as to draw both filtrates separately. The withdrawing rate of the low molecular weight filtrate was set to 0.45 l/h while return rate of the polymer-containing filtrate was set to 0.05 l-h. When the sum of both filtrates reached 0.5 l, filtration was stopped. The culture was continued for 30 days in exactly the same way as in Example 1. Table 4 shows the living cell concentration, the survival ratio and the pressure loss at the time of filtration.

A high cell concentration was reached while maintaining a high survival ratio in the same way as in Examples 1 through 3. The reason why the viable cell concentration was higher than the foregoing Examples was brought by the effect that polymeric growth factors excreted by the cells were recovered.

TABLE 4

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 4.0 | 4.3 | 4.9 | 18 | 45 | 92 | 110 |
| Survival ratio (%) | 91 | 91 | 91 | 92 | 92 | 92 | 92 |
| Pressure drop* at time of filtration (kg/cm$^2$) | −0.07 | −0.07 | −0.07 | −0.07 | −0.06 | −0.06 | −0.08 |

*pressure difference between inner pressure of molecular filtration film and outer pressure of precision filtration film

COMPARATIVE EXAMPLE 1:

The culture of the JTC-1 strain was carried out by use of the culturing system in which a seed cell suspension was prepared in the same way as in Example 1, and the medium had the same composition as that of Example 1.

This culturing system was produced by removing the sparger 9 and the defoaming layer 8 of the filtration-separation apparatus of the system of Example 1 and by adding a stirring blade 3 for stirring the suspension. The operation method was the same as that of the above Example 1 of the invention.

The results are tabulated in Table 5. In comparison with Examples 1~4, clogging occurred more greatly and the pressure loss increased more greatly, and the culture was stopped on the 20th day. Both the viable cell concentration and survival ratio were smaller than those of Examples due to the cell aggregation to the membranes.

TABLE 5

| Item | Days of culture (days) | | | | | |
|---|---|---|---|---|---|---|
| | 0 | 1 | 2 | 5 | 10 | 20* |
| Viable cell concentration ($\times 10^5$ cells/ml) | 4.1 | 4.2 | 4.2 | 7 | 10 | 13 |
| Survival ratio (%) | 91 | 90 | 85 | 80 | 71 | 70 |
| Pressure drop at time of filtration (kg/cm$^2$) | −0.05 | −0.1 | −0.3 | −0.5 | −1.2 | −1.6 |

*stop of culture

EXAMPLE 5

Figure 2:
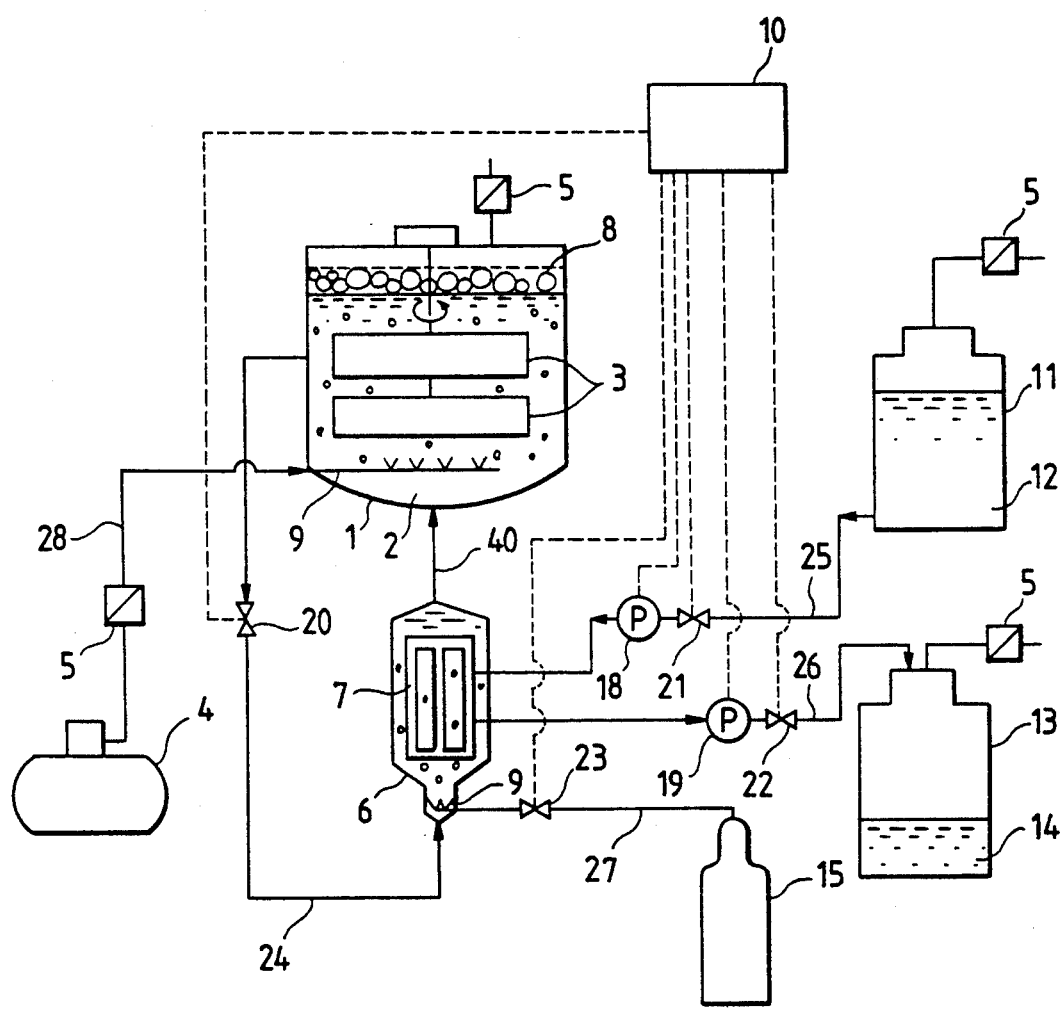

Perfusion culture of animal cells was carried out by use of the culturing system shown in FIG. 2. This system was different from the culturing system of FIG. 1 used in Example 1 in the following points.

1) The filtration apparatus was disposed at the bottom of the culture tank and the upper part of the filtration apparatus was communicated by a transfer piping arrangement 24 so that the culture broth in the filtration apparatus could be sent back to the culture tank due to the gas lifting effects by gas sparging at the bottom of the filtration apparatus. The volume of the filtration apparatus was the same but its upper and lower end portions were contracted so as to effect the rising flow of the solution smoothly.

2) The defoaming layer was not disposed in the filtration apparatus but a defoaming layer of the same kind was disposed on the liquid surface of the culture tank.

3) The supply of oxygen to the culture tank was changed from the overlay system of FIG. 1 to the system for ventilating the gas from a sparger disposed at the bottom of the tank into the broth.

The culturing system of FIG. 2 was steam-sterilized in the same way as in Example 1 and 4.5 l of the medium of the same kind was introduced into the culture tank and the filtration apparatus. Next, 0.5 l of the seed cell suspension prepared in the same way as in Example 1 was inuculated to a fresh medium to make the cell concentration to $3.9 \times 10^5$ cells/ml. Microbial-free air was sparged at a flow rate of 10~30 l/min from the sparger at the bottom of the culture tank and while the bubbles formed on the liquid surface were ruptured by the defoaming layer, culture was carried out at a stirring speed of 20 r.p.m., at 37° C. and pH of 7.0~7.6. The flow rate was adjusted so that the dissolved oxygen concentration (DO) in the culture broth reached 1 ppm.

During the filtration operation, the valve 20 was opened and a circulating flow was formed by the rise of the gas from the sparger 9 disposed below the filtration apparatus. The back-wash of the membrane was repeated for 10 cycles per-day in the same way as in Example 1 and the culture was continued for 31 days. In this instance, the living cell concentration and the survival ratio in the culturing apparatus 1 were lowered and the considerable pressure drop at the time of filtration took place. The drop was caused by the fact that during the filtration, the culture broth was always supplied and circulated from the culture tank to the filtration tank by the contact of bubbles with the membrane and by the gas lift.

TABLE 6

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 4.1 | 4.1 | 4.1 | 15 | 40 | 85 | 98 |
| Survival ratio (%) | 90 | 91 | 91 | 91 | 91 | 91 | 91 |
| Pressure drop at time of filtration (kg/cm$^2$) | −0.03 | −0.03 | −0.03 | −0.04 | −0.04 | −0.04 | −0.04 |

EXAMPLE 6

Perfusion culture of animal cells was carried out by use of the culturing system. In this system, a liquid transfer piping arrangement 17 corresponding to a by-pass was added to the culturing system of Example 5 besides the liquid transfer pipe (not shown) for connecting the culture tank 1 and the bottom of the filtration apparatus 6. A valve 20 and a pump 16 were disposed in this piping arrangement 17 and they were used for compulsively sending back the concentrated cell suspension in the filtration apparatus into the culture tank after back-wash. In this instance, the rate of returning the cell suspension to the culture tank was at a rate of 250 ml/min for 2 minutes. The process of filtration and back-wash was carried out uniformly dividedly 10 cycles per day in the same way as in Example 1 and the culture was continued for 30 days. Table 7 shows the living cell concentration and survival ratio inside the culturing apparatus 1 in this instance and the pressure loss at the time of filtration.

TABLE 7

| Item | Days of culture (days) | | | | | | |
|---|---|---|---|---|---|---|---|
| | 0 | 1 | 2 | 5 | 10 | 20 | 30 |
| Viable cell concentration ($\times 10^5$ cells/ml) | 4.1 | 4.1 | 4.1 | 13 | 42 | 80 | 82 |

TABLE 7-continued

| Item | \multicolumn{7}{c}{Days of culture (days)} | | | | | | |
| --- | --- | --- | --- | --- | --- | --- | --- |
| | 0 | 1 | 2 | 5 | 10 | 20 | 30 |
| Survival ratio (%) | 90 | 90 | 92 | 91 | 92 | 91 | 91 |
| Pressure drop at time of filtration (kg/cm$^2$) | −0.04 | −0.04 | −0.04 | −0.04 | −0.04 | −0.05 | −0.05 |

What is claimed is:

1. A culturing method of living cells comprising the steps of:
   withdrawing a cell culture broth from a culturing apparatus;
   bringing the withdrawn cell culture broth into contact with a membrane for precision filtration wherein said membrane separates the cells present in the culture broth from the filtrate;
   while filtering the cell culture broth through the use of said membrane, bringing a gas which is non-toxic to the cells present in the culture broth into contact with a surface of the membrane immersed in said culture broth to thereby prevent the adherence and propagation of said cells to the membrane surface;
   rupturing the foam occurring on the liquid surface as a result of the addition of the gas to the culture broth by a defoaming layer comprised of a hydrophobic material disposed on the liquid surface;
   returning the cells thus separated from the filtration to said culturing apparatus; and,
   withdrawing the separated filtrate from said culturing apparatus.

2. A culturing method of living cells according to claim 1, wherein said cells are returned to said culture apparatus by back-washing the membrane with a liquid medium.

3. A culturing method of living cells according to claim 1, wherein said filtration membrane is a two-layered tubular membrane comprised of a hollow fiber for precision filtration and a hollow fiber for molecular filtration disposed in said precision filtration hollow fiber in such a manner that a gap is formed between said fibers.

4. A culturing method of living cells according to claim 1, wherein the culture broth in the culture apparatus is brought intermittently to said filtration apparatus during the filtration operation.

5. A culturing method of living cells according to claim 1, wherein said culture broth in said culture apparatus is transferred into said filtration apparatus in a volume of at least 50% of said medium for back-wash.

6. A culturing system for living cells, which comprises:
   a) a culturing apparatus having a vessel for culturing cells in the suspension state in a culture broth;
   b) means for supplying culturing cells into the vessel;
   c) means for supplying a medium into the vessel thereby forming the culture broth containing the culturing cells;
   d) means for withdrawing a part of the culture broth from the vessel;
   e) means for transferring the withdrawn culture broth to a filtration apparatus having a membrane for precision filtration wherein the membrane separates the cells in the culture broth from the filtrate;
   f) means for bringing a gas which is non-toxic to the cells present in the culture broth into contact with the surface of the membrane of the filtration apparatus to thereby prevent adherence and propagation of the cells to the membrane;
   g) means for rupturing the foam occurring on the surface of the culture broth in the filtration apparatus due to the addition of the gas to the culture broth;
   h) means for returning the cells separated from the filtrate in the filtration apparatus to the vessel; and,
   i) means for withdrawing the filtrate from the filtration apparatus.

7. The culturing system according to claim 6, wherein the membrane is a hollow fiber.

8. A culturing system of living cells according to claim 6, wherein the membrane is composed of a tubular membrane for precision filtration and a tubular membrane for melecular filtration disposed in the precision filtration membrane in such a manner that a gap is formed therebetween.

9. A culturing system of living cells according to claim 6, further comprising a washing mechanism for supplying a liquid to the surface of the means for breaking the foam.

10. The culturing system according to claim 6, wherein the filtration apparatus is disposed below the top level of the culture broth in the vessel.

* * * * *